United States Patent
So et al.

(10) Patent No.: US 7,854,826 B2
(45) Date of Patent: Dec. 21, 2010

(54) CARBON NANOTUBE BIOSENSORS WITH APTAMERS AS MOLECULAR RECOGNITION ELEMENTS AND METHOD FOR SENSING TARGET MATERIAL USING THE SAME

(75) Inventors: Hye Mi So, Daejeon (KR); Jeong O Lee, Daejeon (KR); Yong Hwan Kim, Daejeon (KR); Ki Hoon Won, Daejeon (KR); Hyun Ju Chang, Daejeon (KR); Beyong Hwan Ryu, Daejeon (KR); Ki Jeong Kong, Daejeon (KR); Young Min Choi, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 17 days.

(21) Appl. No.: 11/952,310

(22) Filed: Dec. 7, 2007

(65) Prior Publication Data
US 2008/0094078 A1 Apr. 24, 2008

Related U.S. Application Data

(63) Continuation-in-part of application No. PCT/KR2005/004372, filed on Dec. 19, 2005.

(30) Foreign Application Priority Data
Jun. 28, 2005 (KR) .................... 10-2005-0056195

(51) Int. Cl.
C12M 1/00 (2006.01)
C12N 11/00 (2006.01)

(52) U.S. Cl. ............... 204/403.01; 204/403.02; 204/403.03; 204/403.04; 204/403.05; 205/792

(58) Field of Classification Search ............. 204/403.01–403.15; 205/777.5, 778, 792; 436/62–71, 436/500–548
See application file for complete search history.

(56) References Cited

U.S. PATENT DOCUMENTS

| 2003/0013672 A1* | 1/2003 | Lee et al. ............... 514/44 |
| 2003/0022853 A1* | 1/2003 | Erikson et al. .......... 514/44 |
| 2004/0200734 A1* | 10/2004 | Co et al. ............. 205/777.5 |

* cited by examiner

*Primary Examiner*—Nam X Nguyen
*Assistant Examiner*—Susan Thai
(74) *Attorney, Agent, or Firm*—Frommer Lawrence & Haug LLP; Ronald R. Santucci

(57) ABSTRACT

The present invention relates to a carbon nanotube transistor biosensor with aptamers and a method for detecting a target material using the same, more particularly to a carbon nanotube transistor biosensor recognizing the target material, i.e., a specific molecule (such as a protein, a peptide, an amino acid, and an organic/inorganic compound) by using DNA aptamers and a method for screening a target material using the same. In the biosensor of the present invention, the aptamers binding specifically to a particular protein are adsorbed on a carbon nanotube constituting the channel domain of carbon nanotube transistor to easily detect/identify a particular protein via the electric conductivity of carbon nanotube that varies if the particular protein is exposed to corresponding aptamers.

18 Claims, 4 Drawing Sheets

CARBON NANOTUBE BIOSENSORS WITH APTAMERS AS MOLECULAR RECOGNITION ELEMENTS AND METHOD FOR SENSING TARGET MATERIAL USING THE SAME

CROSS-REFERENCE TO RELATED APPLICATIONS

This application is a continuation-in-part of international application number PCT/KR2005/004372 filed Dec. 19, 2005, which was published on Sep. 13, 2007 under publication number WO 2007/102629 A1 and which claims priority of Korean Patent Application Number 10-2005-0056195 filed Jun. 28, 2005, the entire disclosures of which are hereby incorporated by reference.

TECHNICAL FIELD

The present invention relates to a carbon nanotube transistor biosensor with aptamers and a method for sensing a target material using the same, more particularly to a carbon nanotube transistor biosensor recognizing a specific protein by using DNA aptamers, wherein the aptamers that bind specifically to a particular protein are adsorbed on a carbon nanotube constituting the channel domain of the carbon nanotube transistor to easily detect/identify a particular protein by means of variation in the electric conductivity of the carbon nanotube when the protein is exposed to corresponding aptamers and a method for screening a specific molecule using the same.

BACKGROUND ART

Conventionally, a carbon nanotube (CNT) refers to an allotrope of carbon which is abundantly present on earth. CNT is a tube-shaped material wherein one carbon atom binds to another carbon atom thereby forming a hexagonal honeycomb structure. It also refers to an extremely tiny material with a diameter of its tube being a few nanometers (nm=1/1,000,000,000).

Carbon nanotubes in general have excellent mechanical property, electrical property, ability to discharge electric field and hydrogen storing ability with high efficiency. It is known as a nearly perfect material having almost no defects. Carbon nanotubes can be manufactured by using an advanced synthetic technique such as electric discharge method, a pyrolytic method, laser-mediated vacuum evaporation, chemical evaporation by plasma, thermo-chemical evaporation, an electrolytic method, and flame synthesis.

In practice, carbon nanotubes may be applied to almost all fields including astronautics, bioengineering, environmental energy, material industry, pharmaceuticals, pharmaceutical medicines, electronic computers, securities and the like. For example, a carbon nanotube transistor is one of the carbon nanotube products.

The carbon nanotube transistor is composed of a source, a drain and a gate, wherein its channel domain is made of a carbon nanotube.

Carbon nanotube constituting the channel domain of the above carbon nanotube transistor has a few advantages as follows. First, it has excellent electric and thermal conductivities while maintaining the properties of a semiconductor or a metal, thus having a highly efficient heat emission. Further, carbon nanotubes are light-weighted but have mechanical strength 100 times stronger than that of steel, hardly react with other compounds due to their unique chemical properties thus enabling a very stable operation of electronic elements. Therefore, researches have been focused on developing new applied elements and such efforts have been extended recently to medical and biotechnological fields.

Due to the recent trend of aging society and extended life span of people worldwide, there has been a growing concern on the importance of how to manage a healthy individual life. Accordingly, the necessities for an early diagnosis of severe diseases such as cancers and other life-threatening diseases have been emphasized and thus it has been in urgent need to develop a medical device/equipment for frequent self-diagnosis of medical conditions with reduced cost and time, whenever deemed necessary. In this context, it appears very important to find a method to detect and identify the presence of any specific molecules (such as proteins, peptides, amino acids and organic/inorganic compounds) in human serums, urines and the like.

Many researchers have since then made various efforts to develop novel diagnostic and therapeutic techniques, and the formidable amount of biological information acquired from the completion of global Human Genome Project is now being combined with nanotechnologies. Especially, the carbon nanotubes and semiconductor nanowires are being applied to manufacture a highly sensitive biosensor by using their electric features.

To date, diagnostic sensors using antigen-antibody reaction have been overwhelming in the biosensors market. The antigen-antibody reaction is a highly valuable tool to diagnose diseases with accuracy due to its superior specificity. However, the above method has a disadvantage that antibodies consist of proteins. In detail, certain antibodies are very difficult to produce since they require a very complicated condition of culture and synthesis. Further, the characteristics of antibodies may slightly differ from each another depending upon the batches from which they are prepared and they are also too expensive to be distributed widely for commercial use.

Further, the biosensors using the antigen-antibody reaction are much restricted in terms of their valid length of distribution due to stability problem. The unstable nature of proteins increases the unit production cost and may also generate errors in a diagnostic sensor during operation.

Therefore, there is a need to develop a new diagnostic sensor which has an excellent stability and cost-effectiveness while having an excellent substrate-specificity comparable to or even greater than that of antibodies.

DISCLOSURE OF INVENTION

In an effort to resolve the above-mentioned problems, the present inventors have succeeded in providing a carbon nanotube transistor biosensor using an aptamer, wherein the aptamer, a single-stranded DNA (or RNA) oligomer having high affinity for a protein, is adsorbed as a probe on the surface of carbon nanotubes constituting a channel domain of the carbon nanotube transistor to detect a target material, a particular protein binding specifically to the aptamer; and a method for screening the target material using the same.

Therefore, in an embodiment of the present invention, there is provided a carbon nanotube transistor biosensor using an aptamer, wherein the aptamer, a single-stranded DNA/RNA oligomer binding specifically to a certain molecule (such as a protein, a peptide, an amino acid and an organic/inorganic compound) is adsorbed on a one-dimensional conductor carbon nanotube having a long elastic scattering length and distance of phase dispersion to easily detect/identify the presence of a particular protein via the electric resistance of carbon nanotube which varies when the particular protein is bound to corresponding aptamers.

Aptamers are artificial oligonucleotides (DNA or RNA) that can bind to a wide variety of entities (e.g., metal ions, small organic molecules, proteins, and cells) with high selectivity, specificity and affinity, equal to or often superior to those of antibodies. These aptamers can be isolated from combinatorial nucleic acid libraries using in vitro selection methods. Synthesizing aptamers is relatively inexpensive, and they can be engineered easily for immobilization purposes. Moreover, unlike proteins, which are irreversibly denatured in unfavorable conditions, aptamers are capable of reversible denaturation. Consequently, by incorporating these aptamers into biosensors, it is possible to subject these sensing elements to repeated use, thereby realizing a device that is potentially recyclable.

The biggest merit of using DNA (RNA) aptamers in FET type sensors lies in their small size. In the case of immunological field effect transistors (ImmunoFETs), which use an antibody-antigen binding recognition step, there is a high possibility that the recognition binding occurs outside the electrical double layer in physiological salt concentrations. In this respect, the antibody (~10 nm) is much larger than the electrical double layer, such that most of the protein charges will be at a distance greater than the Debye length (~3 nm in 10 mM ionic concentrations), making them impossible to detect. Since aptamers (1~2 nm) are much smaller than protein antibodies, it is possible that the aptamer-protein binding event can occur inside the electrical double layer in millimolar salt concentrations.

Moreover, as was confirmed by the present invention, carbon nanotube biosensor with aptamers as recognition elements can be recycled. Unlike antibodies, which are essentially proteins, aptamers can undergo reversible conformational change under high salt concentrations or heat. Aptamers lose their 3-dimensional conformations under high salt concentrations, then already bound target molecules (such as proteins, peptides, amino acids and organic/inorganic compounds) can be released from aptamer. Therefore, by simply washing the sensor with high salt solutions, the sensor can be used again. In case of sensors utilizing antibodies as recognition elements, this kind of treatment can irreversibly damage antibodies, so they can only be used for disposable sensors.

In another embodiment of the present invention, there is provided a method for screening a target material using the above carbon nanotube transistor biosensor.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

In one preferred embodiment, the present invention provides a carbon nanotube transistor biosensor using an aptamer, which comprises a carbon nanotube transistor having a source, a drain, a gate and a carbon nanotube constituting a channel domain; a DNA or RNA aptamer immobilized on the surface of a carbon nanotube as a recognition element; and a linker to immobilize the aptamer on the carbon nanotube.

Preferably, the channel composed of carbon nanotubes made of a single-walled carbon nanotube or a multi-wall carbon nanotube.

Preferably, the channel composed of carbon nanotubes can be selected from the group consisting of various nanowires of metal oxides and semiconductor nanowires having the excellent feature of a transistor.

In the present invention, the nanowire constituting the channel can employ an aptamer as a molecular recognition element regardless of its kinds.

Preferably, the nanowire has less than 50 nm of diameter. More preferably, the single-walled carbon nanotube can be a carbon nanotube having less than 2 nm of diameter and the multi-walled carbon nanotube can be a carbon nanotube having less than 50 nm of diameter.

Preferably, the material that used to immobilize the aptamer on the surface of carbon nanotube is at least the one selected from pyrene and any other molecules with high affinity for the carbon nanotube. The example of pyrene may contain 1-pyrenebutyric acid N-hydroxysuccinimide ester.

More preferably, one hydrophobic portion of the adhesive material is adsorbed on the carbon nanotube while the other portion of fixing material is covalently bonded to the aptamer. In another preferred embodiment, the present invention provides a method for detecting a target material by using the biosensor, which comprises steps of:

(a) manufacturing a carbon nanotube transistor, wherein an aptamer is immobilized onto a carbon nanotube, which constitutes the channel domain of said carbon nanotube transistor, to provide a structure for its binding to a target material;

(b) measuring the change in electric conductivity of said carbon nanotube in the event said target material, which specifically binds to said aptamer, is exposed to said aptamer; and (c) detecting/identifying said target material based on the change in electric conductivity.

Preferably, the target material is at least one selected from the group consisting of proteins, peptides, amino acids, nucleotides, drugs, vitamins, organic compounds, inorganic compounds and the like.

Hereinafter, the present invention will be described more clearly with reference to the appended drawings as set forth hereunder.

Figure 1:
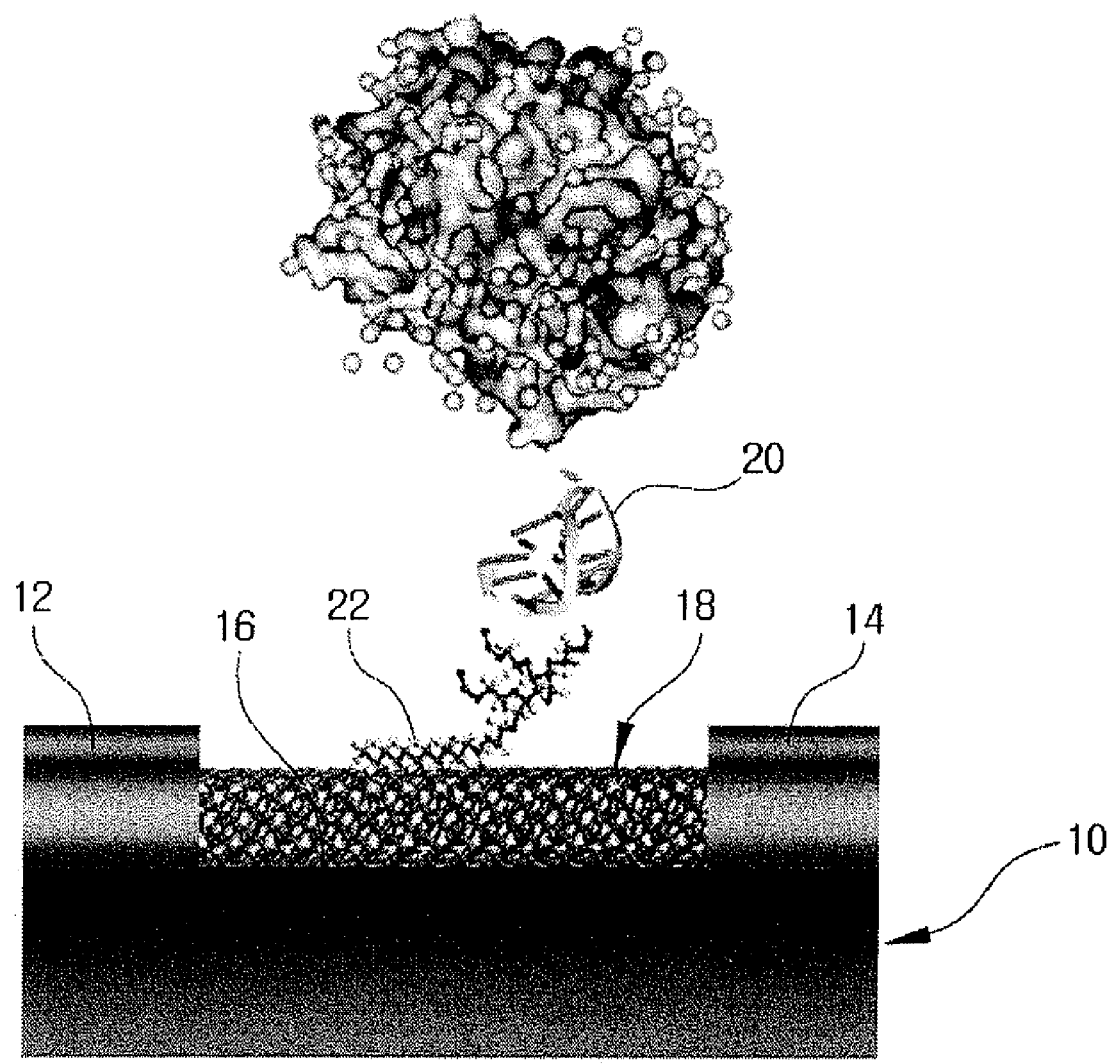
FIG. 1 shows an overall view of a biosensor using a DNA aptamer and a carbon nanotube transistor according to the present invention.
Figure 2:
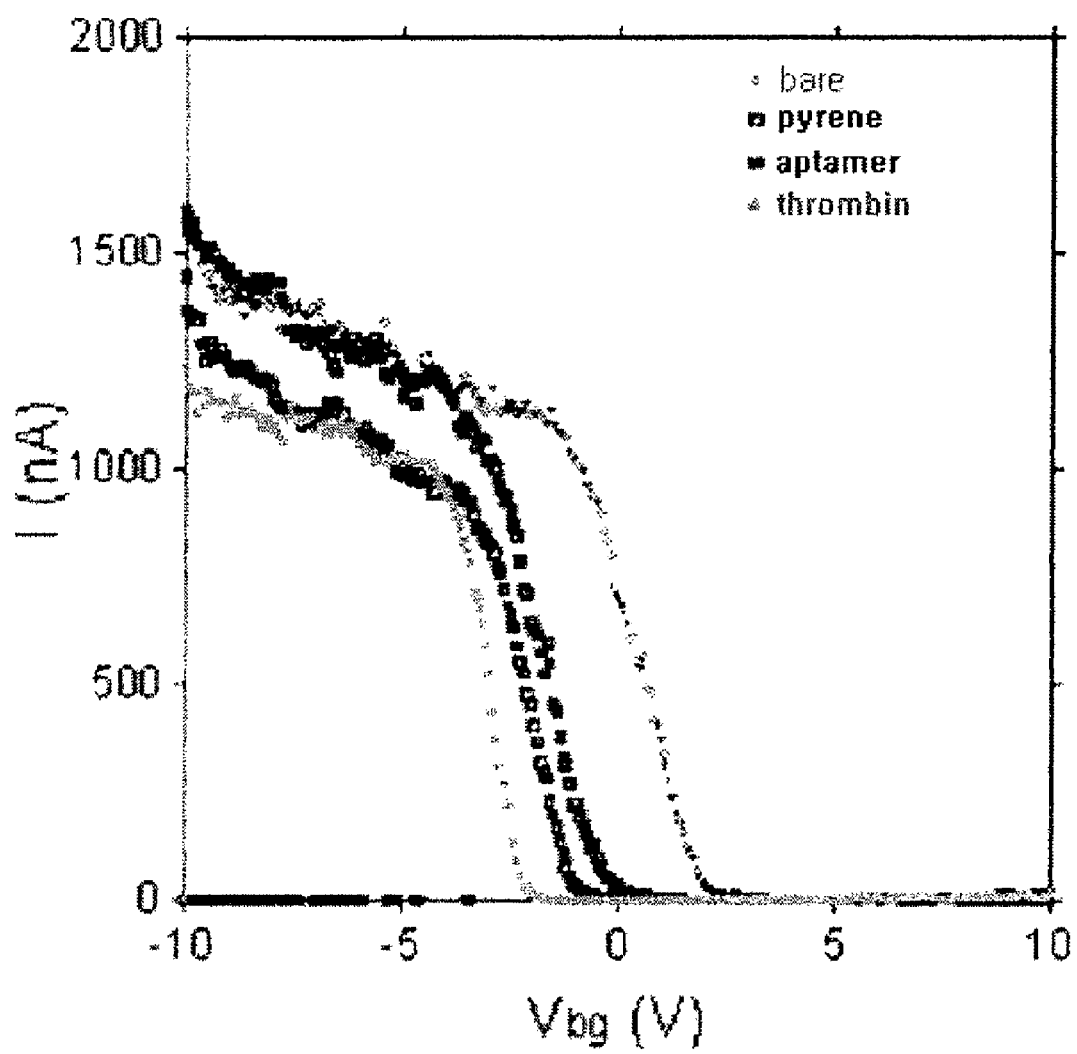
FIG. 2 shows the electric current variation of transistor when reacting an aptamer with thrombin in a preferred embodiment of biosensor using a DNA aptamer and a carbon nanotube transistor according to the present invention.

FIG. 1 shows the overall view of biosensor using a DNA aptamer and a carbon nanotube transistor according to the present invention.

The biosensor of the present invention has a main feature to modify a carbon nanotube transistor by immobilizing DNA aptamers on the surface of carbon nanotube. As a consequence, the biosensor of the present invention retains the excellent sensitivity and selectivity so as to recognize even a single viral particle, a small organic molecule and a single protein and to measure even a relatively low concentration of a particular molecule, and further, can selectively sort out specific molecules. Moreover, due to the reversible conformation of aptamers, regeneration of the biosensor can be accomplished.

As described above, the carbon nanotube transistor 10 consists of a source 12, a drain 14 and a gate 16 as in a conventional transistor, but a carbon nanotube 18 is applied to prepare a channel domain of the transistor.

In the basic structure of the carbon nanotube transistor, a DNA aptamer 20 is immobilized on the surface of the carbon nanotube 18 by using a fixing material 22.

The aptamer 20 is a single-stranded DNA or RNA oligomer that can to bind specifically to a particular molecule (such as a protein, a peptide, an amino acid and an organic/inorganic compound). It is expected to substitute an antibody which has a disadvantage in its biochemical nature. The aptamer has several advantages to retain intrinsic affinity, specificity and selectivity. It may satisfy user's need to recognize specific molecules in biotechnological fields.

Preferably, the material 22 that immobilizes the aptamer 20 on the surface of the carbon nanotube 18 can be a cross-linker having affinity for the carbon nanotube 18. Due to the hydrophobic property of the carbon nanotube 18, one hydrophobic portion of the cross-linker is adsorbed on the carbon nanotube 18 while the other portion of the cross-linker is covalently bonded to the aptamer 20.

More preferably, the material 22 that immobilizes the aptamer 20 on the surface of the carbon nanotube 18 can be pyrene including 1-pyrenebutyric acid N-hydroxysuccinimide ester, and further selected from any other molecules with high affinity for the carbon nanotube.

Preferably, the channel domain composed of the carbon nanotube 18 can be made of a single-walled carbon nanotube or a multi-walled carbon nanotube. More preferably, the single-walled carbon nanotube can be a carbon nanotube having less than 2 nm of diameter and the multi-walled carbon nanotube can be a carbon nanotube having less than 50 nm of diameter.

As illustrated above, the aptamer 20 can be used to detect a target material, if adsorbed on the surface of the carbon nanotube 18 in the carbon nanotube transistor 10. That is, the target material can be identified by sensing the variation of electric conductivity in the carbon nanotube 18, when it is exposed bound to the corresponding aptamer 20.

Preferably, the target material binding with aptamer 20 can be selected from the group consisting of proteins, peptides, amino acids, nucleotides, drugs, vitamins, organic compounds, inorganic compounds and the like.

Therefore, the target material, especially the presence and the absence of particular protein, can be detected/identified easily by measuring the electric variation in the carbon nanotube 18 while the particular protein is exposed bound to the corresponding aptamer 20.

EXAMPLES

Practical and presently preferred embodiments of the present invention are illustrated as shown in the following Examples.

However, it will be appreciated that those skilled in the art, on consideration of this disclosure, may make modifications and improvements within the Example In order to recognize a specific molecule, the aptamers binding specifically to the molecule were adsorbed on the surface of carbon nanotube constituting the channel domain of a carbon nanotube transistor with linker. In practice, 1-pyrenebutyric acid N-hydroxysuccinimide ester was utilized to fix immobilize the aptamers on the carbon nanotube and then to modify the surface.

In detail, one end of 1-pyrenebutyric acid N-hydroxysuccinimide ester was adsorbed on the carbon nanotube while the other end of 1-pyrenebutyric acid N-hydroxysuccinimide ester was reacted with the aptamer to fix immobilize the aptamers on the carbon nanotube.

Figure 3:
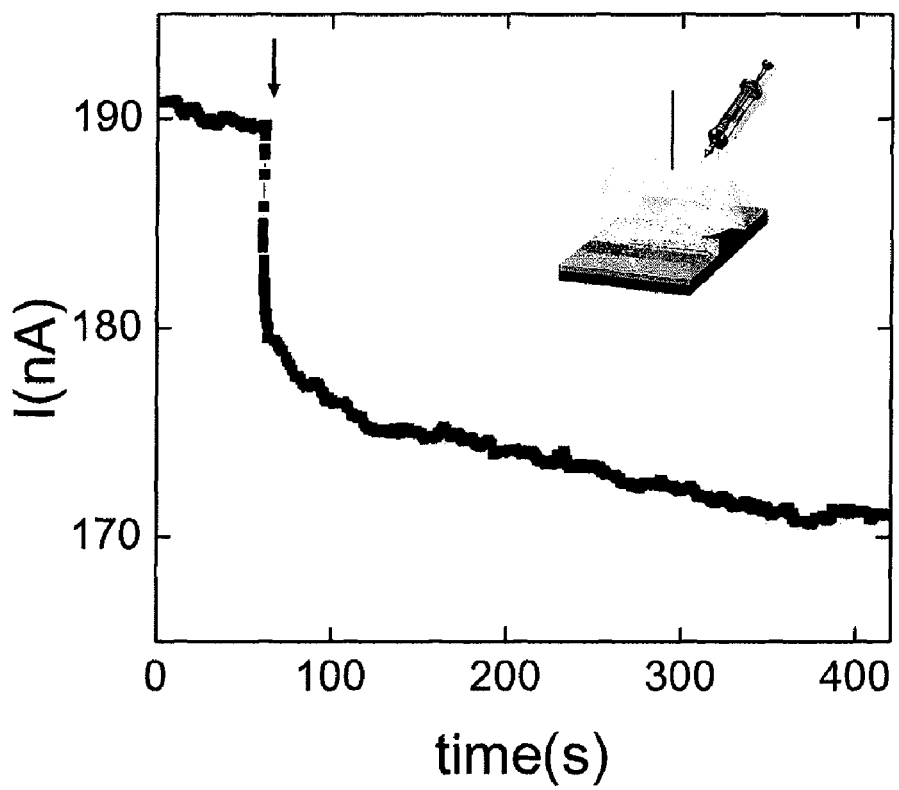
FIG. 3 shows the real-time variation of electric current in a transistor when reacting an aptamer with thrombin in a preferred embodiment of biosensor using a DNA aptamer and a carbon nanotube transistor according to the present invention.

Then, thrombin, a protease participating in blood coagulation was reacted with the aptamers immobilized with 1-pyrenebutyric acid N-hydroxysuccinimide ester and examined to measure the electric variation before and after the reaction. FIG. 3 shows the real-time data measurement of electric current in a transistor.

In detail, the bias of source-drain electrode was predetermined at 1 V and the electric voltage of the gate was varied. The result of the gate was illustrated in FIG. 3: blue line indicates data reacting with 1-pyrenebutyric acid N-hydroxysuccinimide ester; green line indicates data of aptamers; and yellow line indicates data of thrombin. Consequently, the gate threshold voltage is observed to move to the right direction after fixing the aptamers, because the backbone of the DNA aptamer containing negative charges induced a doping effect.

Figure 4:
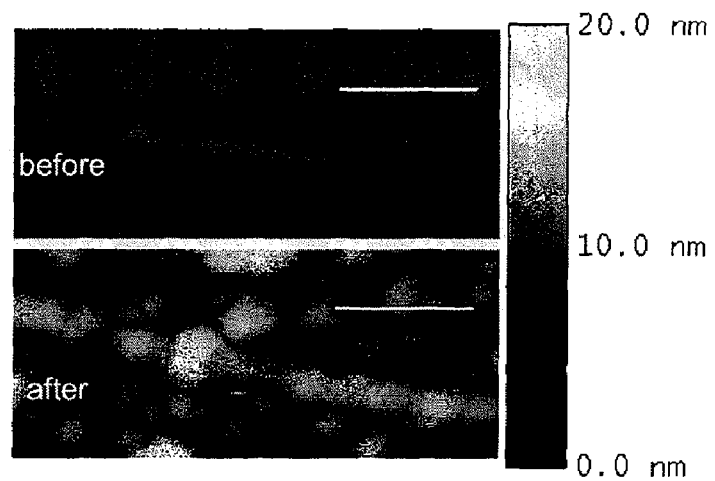
FIG. 4 shows the AFM observation of elements after reacting them with thrombin according to the present invention.

FIG. 4 illustrates the real-time observation obtained by the procedure: (1) adsorbing the aptamers on the carbon nanotube by using CDI-tween 20 as a fixing material; and (2) reacting thrombin with the aptamers. FIG. 4 shows the AFM image of elements after the reaction.

Therefore, the electric conductivity is identified to decrease in the carbon nanotube transistor right after reacting thrombin on the aptamers.

Figure 5:
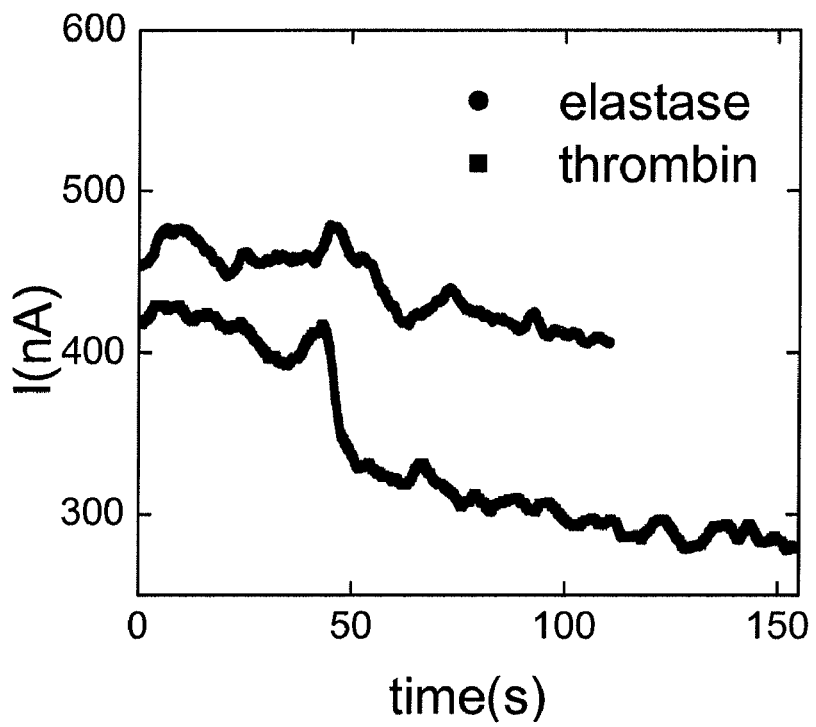
FIG. 5 shows the selectivity of thrombin aptamer-immobilized carbon nanotube transistor sensor.

FIG. 5 shows the selectivity of carbon nanotube biosensor with thrombin aptamers as recognition elements. As shown in the graph, the sensor did not show noticeable changes upon reaction with elastase. Elastase is a family protein of thrombin, and they have almost identical molecular weights and isoelectric point. Then, when the same sensor react with thrombin, abrupt decrease of conductance observed from the device.

Figure 6:
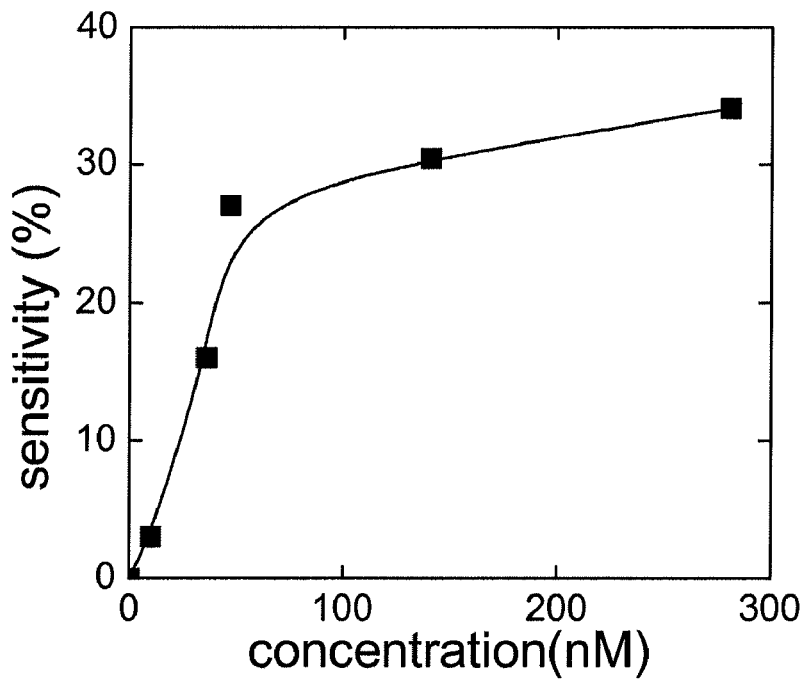
FIG. 6 shows the sensitivity of thrombin aptamer-immobilized carbon nanotubes transistor sensor.

FIG. 6 shows the sensitivity of carbon nanotubes biosensor with thrombin aptamers as recognition elements. The sensitivity was defined as $\Delta I/I$, and sensor was regenerated at each point by washing them with 6 M guanidine hydrochloride solutions.

As confirmed above, if a recognition element detecting a specific protein associated with a specified disease is adsorbed on the surface of carbon nanotube, the specific protein existing in blood may bind to the recognition element on the surface and changes the electric conductivity on the carbon nanotube. Then, the resulting electric signal sensing the electric change is estimated to detect/identify the specific protein as a disease marker.

INDUSTRIAL APPLICABILITY

As illustrated and confirmed above, a carbon nanotube transistor biosensor using DNA aptamers and a method for screening target material using the same according to the present invention have attained advantageous effects that the presence of particular protein can be detected/identified easily through the variation of electric conductivity in a carbon nanotube, when the particular protein is exposed to the corresponding aptamers adsorbed on the surface of the carbon nanotube constituting the channel domain of the carbon nanotube transistor.

Such an electric measurement using the biosensor of the present invention can be applied to construct an integrated system and a portable diagnostic system even in a low cost. Further, it is advantageous to accelerate the development of nano biosensors.

Especially, the biosensor constructed of a highly sensitive carbon nanotube and a selective DNA aptamer can detect/identify the presence and the absence of particular molecules (such as proteins, peptides, amino acids and organic/inorganic compounds) in blood and the like for early diagnosis and efficient treatment of diseases. Moreover, as was confirmed by the present invention, carbon nanotube biosensor with aptamers as recognition elements can be recycled. Unlike antibodies, which are essentially proteins, aptamers can undergo reversible conformational change under high salt concentrations or heat. Aptamers lose their 3-dimensional conformations under high salt concentrations, then already bound target molecules (such as proteins, peptides, amino acids and organic/inorganic compounds) can be released from aptamer. Therefore, by simply washing the sensor with high salt solutions, the sensor can be used again. In case of sensors utilizing antibodies as recognition elements, this kind of treatment can irreversibly damage antibodies, so they can only be used for disposable sensors.

Those skilled in the art will appreciate that the conceptions and specific embodiments disclosed in the foregoing description may be readily utilized as a basis for modifying or designing other embodiments for carrying out the same purposes of the present invention.

What is claimed is:

1. A carbon nanotube transistor biosensor using a single stranded DNA or single stranded RNA aptamer, comprising:
   (a) a carbon nanotube transistor comprising a source, a drain, and a gate, and a channel domain which consists of a carbon nanotube;
   (b) a single stranded DNA or single stranded RNA aptamer immobilized on the surface of said carbon nanotube for molecular recognition, and
   (c) a linker material to immobilize aptamers on the surface of a carbon nanotube;
   wherein said carbon nanotube transistor biosensor contains an electrical double layer.

2. The carbon nanotube transistor biosensor using an aptamer according to claim 1, wherein said channel domain consisting of the carbon nanotube is made of a single-walled carbon nanotube or a multi-walled carbon nanotube.

3. The carbon nanotube transistor biosensor using an aptamer according to claim 1, wherein said channel domain consisting of the carbon nanotube is a nanowire of various metal oxides or a semiconductor nanowire having a feature of a transistor.

4. The carbon nanotube transistor biosensor using an aptamer according to claim 3, wherein said nanowire constituting said channel domain recognizes the aptamer as a molecular recognition element and having a diameter of less than 50 nm.

5. The carbon nanotube transistor biosensor using an aptamer according to claim 2, wherein said single-walled carbon nanotube has a diameter of less than 2 nm and said multi-walled carbon nanotube has a diameter of less than 50 nm.

6. The carbon nanotube transistor biosensor using an aptamer according to claim 1, wherein the aptamer is selected from single-stranded DNAs.

7. The carbon nanotube transistor biosensor using an aptamer according to claim 1, wherein the aptamer is selected from single-stranded RNAs.

8. A method for detecting a target material by using the biosensor of claim 1 comprising:
   (a) manufacturing a carbon nanotube transistor, wherein a single stranded DNA or a single stranded RNA aptamer is immobilized onto a carbon nanotube, which constitutes the channel domain of said carbon nanotube transistor, to provide a structure for its binding to a target material;
   (b) measuring the change in electric conductivity of said carbon nanotube in the event said target material, which specifically binds to said aptamer, is exposed to said aptamer; and
   (c) detecting/identifying said target material based on the change in electric conductivity wherein the binding of the aptamer and detecting/identifying of said target material occurs inside the electrical double layer of the biosensor.

9. The method for detecting a target material by using the biosensor of claim 8 wherein said target material is at least one selected from the group consisting of proteins, peptides, amino acids, nucleotides, drugs, vitamins, organic compounds and inorganic compounds.

10. The method for detecting a target material by using the biosensor of claim 8 wherein the sensor can be regenerated and recycled owing to the reversible conformational changes in aptamers.

11. The carbon nanotube transistor biosensor using an aptamer according to claim 4, wherein said linker material immobilizing the aptamer onto the surface of said carbon nanotube is selected from pyrene and a molecule with affinity for the carbon nanotube.

12. The carbon nanotube transistor biosensor using an aptamer according to claim 11, wherein one hydrophobic portion of said linker material is adsorbed on the carbon nanotube while the other portion of said linker material is covalently bonded to the aptamer.

13. The carbon nanotube transistor biosensor using an aptamer according to claim 12, wherein the linker material is 1-pyrenebutyric acid N-hydroxysuccinimide ester.

14. The carbon nanotube transistor biosensor using an aptamer according to claim 13, wherein the aptamer is reactive with thrombin.

15. The carbon nanotube transistor biosensor using an aptamer according to claim 5, wherein said linker material immobilizing the aptamer onto the surface of carbon nanotube is selected from pyrene and a molecule with affinity for the carbon nanotube.

16. The carbon nanotube transistor biosensor using an aptamer according to claim 15, wherein one hydrophobic portion of said fixing linker material is adsorbed on the carbon nanotube while the other portion of said linker material is covalently bonded to the aptamer.

17. The carbon nanotube transistor biosensor using an aptamer according to claim 16, wherein the linker material is 1-pyrenebutyric acid N-hydroxysuccinimide ester.

18. The carbon nanotube transistor biosensor using an aptamer according to claim 17, wherein the aptamer is bindable with thrombin.

* * * * *